United States Patent [19]

O'Brien et al.

[11] Patent Number: 4,996,317

[45] Date of Patent: Feb. 26, 1991

[54] CAFFEINE RECOVERY FROM SUPERCRITICAL CARBON DIOXIDE

[75] Inventors: Michael J. O'Brien, Port Monmouth; Jean E. Spence, Bogota; Ronald H. Skiff, Edison, all of N.J.; Gerald J. Vogel, Carrollton, Tex.; Ravi Prasad, Midlothian, Va.

[73] Assignee: Kraft General Foods, Inc., Glenview, Ill.

[21] Appl. No.: 229,369

[22] Filed: Aug. 5, 1988

[51] Int. Cl.$^5$ .................................................. A23F 5/18
[52] U.S. Cl. ..................................... 544/274; 210/511
[58] Field of Search ................................ 544/274, 275

[56] References Cited

U.S. PATENT DOCUMENTS

| | | |
|---|---|---|
| 2,896,740 | 7/1959 | Drummond . |
| 3,640,054 | 2/1972 | Katz . |
| 4,246,291 | 1/1981 | Prasad et al. .................. 426/387 |
| 4,251,559 | 2/1981 | Margolis et al. .............. 426/490 |
| 4,312,646 | 11/1982 | Fattinger . |
| 4,341,804 | 7/1982 | Prasad et al. .................. 426/387 |
| 4,348,422 | 9/1982 | Zosel ............................. 426/478 |
| 4,472,442 | 9/1984 | Katz .............................. 544/275 |
| 4,820,537 | 4/1989 | Katz .............................. 426/481 |

FOREIGN PATENT DOCUMENTS 0010636A 5/1980 European Pat. Off. .

*Primary Examiner*—Nicholas S. Rizzo
*Attorney, Agent, or Firm*—Thomas A. Marcoux; Thomas R. Savoie; Daniel J. Donovan

[57] ABSTRACT

A process and apparatus for caffeine recovery from supercritical carbon dioxide is disclosed. The process involves countercurrent extraction of caffeine from supercritical carbon dioxide with water at pressures in excess of 1,000 p.s.i. in an unpacked extraction column. The apparatus includes an unpacked extraction vessel having a distributor therein for distributing water throughout substantially the entire cross-sectional area of the vessel.

8 Claims, 3 Drawing Sheets

4,996,317

CAFFEINE RECOVERY FROM SUPERCRITICAL CARBON DIOXIDE

FIELD OF THE INVENTION

The present invention relates to a process and apparatus for recovery of caffeine from supercritical carbon dioxide.

BACKGROUND OF THE INVENTION

One of the known methods of extracting caffeine from green coffee beans is through the use of supercritical carbon dioxide. The supercritical carbon dioxide is contacted with moist green coffee beans at high pressure to extract caffeine therefrom. In these processes it is generally desirable to recirculate the supercritical carbon dioxide and, thus, it is necessary to remove the caffeine from the carbon dioxide so that it may be recirculated.

The commercial method for removing caffeine from supercritical carbon dioxide involves the use of activated carbon. Batch extraction with water is taught by U.S. Pat. No. 3,806,619 issued April 23, 1974 entitled "Process For Recovering Caffeine". Generally the extraction of caffeine from supercritical carbon dioxide must be carried out at high pressure in order to reduce the costly need to change gas pressure. Due to the cost of high pressure equipment, it is also desirable to minimize the size of the vessel used for contact of the extractant and supercritical carbon dioxide. Prior art methods employed high-efficiency packing for liquid counter current extractant of a fluid within a minimum vessel size. The packing, though efficient in contracting the two fluids can show a tendency to foul. Thus, it was often necessary to replace the packing or flush the packing in some manner to clear the fouling. This involved lengthy periods of equipment downtime and high costs. With such high pressure equipment, the necessity of changing packing is cost prohibitive.

Accordingly, there is the need in the prior art for a process and apparatus for extracting caffeine from supercritical carbon dioxide at high pressure in a manner which eliminates fouling of the extraction vessel. In addition, there is a need for a method and apparatus for high-efficiency caffeine removal from supercritical carbon dioxide which is cost-efficient and does not require long periods of downtime for cleaning.

SUMMARY OF THE INVENTION

The present invention relates to a process for the extraction of caffeine from supercritical carbon dioxide. The process comprises countercurrently contacting water with caffeine-containing supercritical carbon dioxide in a column which is substantially open from end to end.

The present invention also relates to an apparatus for recovering caffeine from supercritical carbon dioxide by countercurrent contact with water at a pressure of at least 1000 p.s.i. The apparatus comprises:

- an unpacked elongate extraction vessel having a water inlet and a gas outlet at the upper end and a gas inlet and water outlet at the lower end;
- distributor means for providing water to said extraction vessel from said water inlet at a nozzle velocity of at least 100 ft/min., said distributor means comprising a plurality of spacially separated conduits fluidly connected to said water inlet and each having one or more apertures therein for distributing water to said extraction vessel over a substantial cross-sectional area of said vessel; and
- means for providing caffeine-containing supercritical carbon dioxide to said gas inlet in an amount sufficient to maintain a weight ratio of supercritical carbon dioxide to water in the extraction column of at least 6:1.

One advantage of the present invention is to provide a method and apparatus for recovery of caffeine from supercritical carbon dioxide which is simple and does not require complex internal packing of the extraction vessel and yet achieves the required stages or efficiency of extraction required.

Another advantage of the present invention is to provide a method and apparatus for caffeine recovery from supercritical carbon dioxide which does not require prolonged downtime because of fouling in the extraction vessel.

These and other advantages of the present invention will be apparent to one of ordinary skill in the art from the detailed description which follows.

DETAILED DESCRIPTION OF THE PREFERRED EMBODIMENTS

The present invention relates to a process and apparatus for recovering caffeine from supercritical carbon dioxide. Typically, spray towers used in liquid-liquid extractions give low separation efficiency on the order of one theoretical stage and internal packing is needed to achieve the desired degree of separation in excess of one theoretical stage. However, the present process exhibits a separation efficiency in excess of one theoretical stage without employing internal packing. The process takes advantage of the properties of supercritical carbon dioxide including its low viscosity and low interfacial tension. These properties allow operation of the extraction column at high velocities which are as much as three to four times higher than in normal liquid-liquid extraction columns. Operation at high velocity results in an unexpectedly high separation efficiency in the present process.

Thus, the present invention provides desired caffeine recovery from supercritical carbon dioxide in a simple and highly efficient manner without employing complex internal packing in the extraction vessel. In this way, fouling of the column is minimized or completely eliminated as a result of the absence of internal packing in the column. This results in design, fabrication and operating cost savings as well as increased capacity of a given extraction vessel all due to the lack of obstructions inside the vessel. Thus, if desired, the overall extraction vessel size can be reduced in comparison to a similar vessel employing internal packing without a corresponding reduction in the amount of extraction that can be accomplished in a given unit of time. Finally, separation efficiencies are vastly improved over conventional liquid-liquid extractors and are comparable to packed tower performance levels in similar extraction systems.

Figure 1:
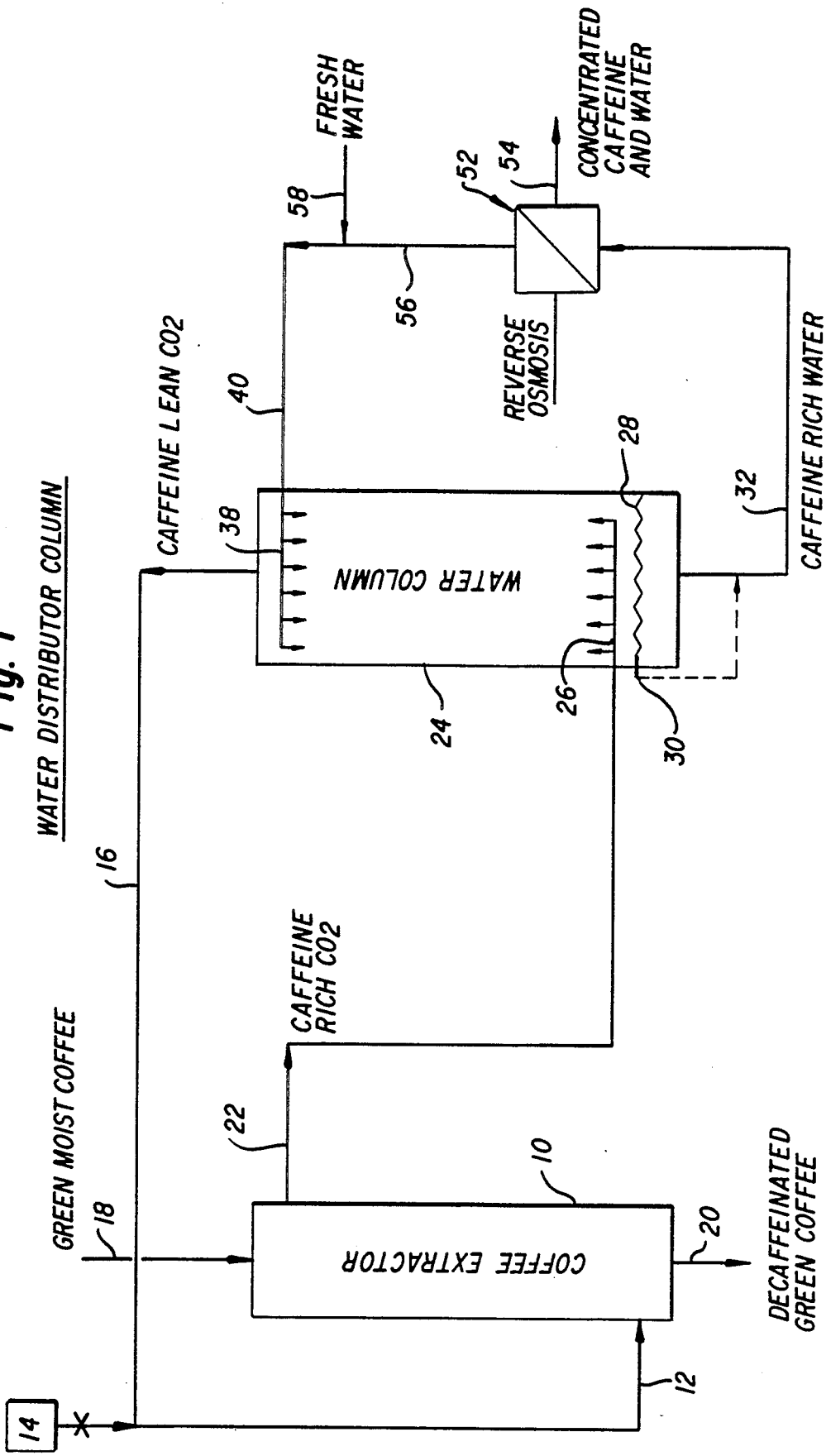
FIG. 1 is a schematic illustration of a decaffeination process embodying the caffeine recovery process of the present invention.

Referring now to FIG. 1, there is shown a schematic representation of a decaffeination process which employs the caffeine recovery process and apparatus of the present invention. The decaffeination apparatus used in this process includes a caffeine extraction vessel 10 wherein supercritical carbon dioxide is contacted with green coffee beans to extract caffeine therefrom. The supercritical carbon dioxide used to extract caffeine from green coffee beans is fed through inlet pipe 12 and may come from either supercritical carbon dioxide source 14, recycle stream 16 or a combination of both. Green coffee beans are supplied to caffeine extraction vessel 10 through bean feeder 18 and they move downwardly through caffeine extraction vessel 10 and are removed through bean outlet 20. Caffeine extraction vessel 10 is shown schematically in FIG. 1, and a more-detailed description of this apparatus can be found in copending application Ser. No. 166,748, filed March 8, 1988, now U.S. Pat. No. 4,820,537 issued April 11, 1989 the disclosure of which is hereby incorporated by reference.

Figure 2:
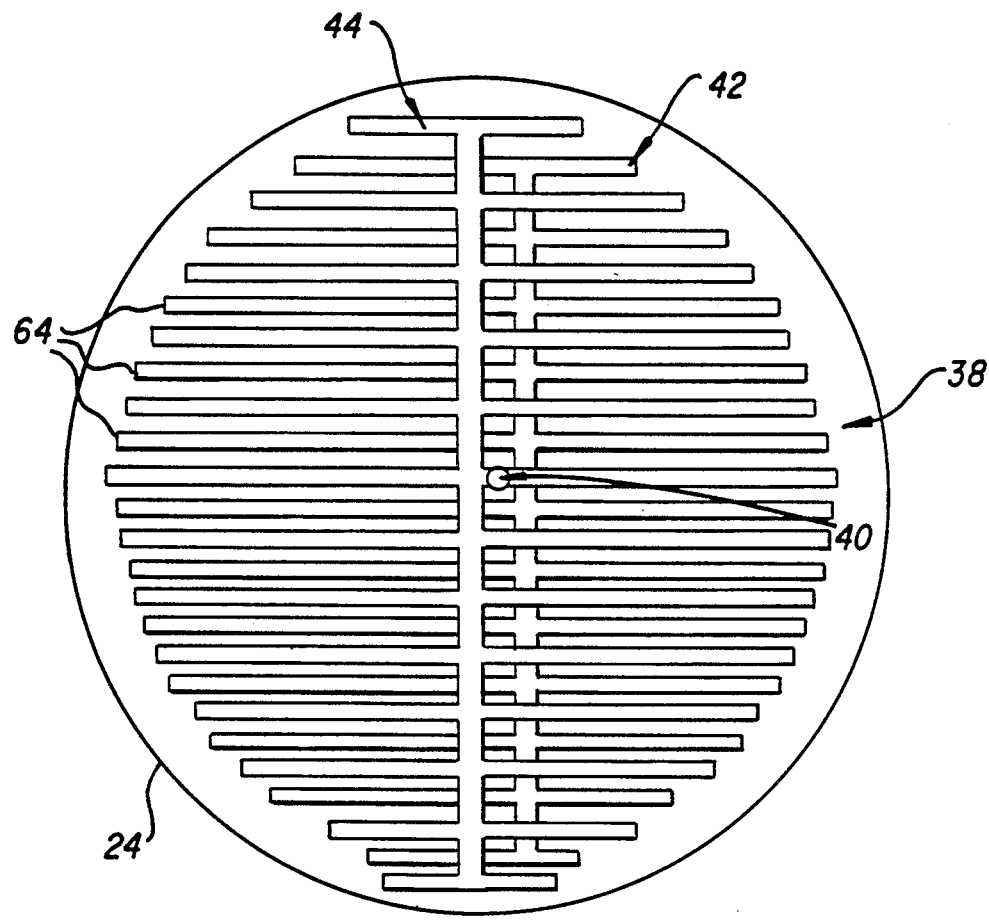
FIG. 2 is a top view of a distributor of the present invention.

The caffeine laden supercritical carbon dioxide is removed from caffeine extraction vessel 10 through gas outlet pipe 22 which leads to water column 24. The supercritical carbon dioxide is fed into the water column 24 by a gas distributor 26. The distributor preferably includes a plurality of opening which may be provided in one or more conduits which extend into the body of the water column. In that event, the conduit perferably occupies a minimum of the cross-sectional area of the column to prevent entrainment of descending water. The caffeine-containing, supercritical carbon dioxide is preferably fed to extraction column 24 above liquid level 28. Liquid level 28 is maintained by liquid sensor 30 which controls the flow of caffeine-rich water through discharge line 32. At the top of extraction column 24 there is located water distributor 38 which distributes water droplets throughout substantially the entire cross-sectional area of extraction column 24. Distributor 38 is connected to water inlet 40. As shown in FIG. 2, distributor 38 preferably includes two tiers of distributor pipes: an upper tier 42 and a lower tier 44, connected by conduit 46.

Caffeine-rich water from absorber column 24 is then treated at 52 to remove caffeine. Removal of caffeine may be effected at a pressure which is substantially lower then the generally high pressure Prevailing in columns 10 and 24. In that event, the pressure of the water in line 32 is reduced prior to treatment for separation of caffeine.

Caffeine may be removed from water stream 32 in any convenient manner such as distillation, absorption, membrane separation, and the like, but is preferably effected by reverse osmosis, in which event there is produced a retentate stream 54 having a concentration of caffeine which is higher than that in stream 32 and a permeate stream 56 having a reduced caffeine concentration. A preferred reverse osmosis system for use in the present invention is described in co-pending application Ser. No. Case 3661 filed on even date entitled "Method For Decaffeinating Coffee Materials Including A Reverse Osmosis Permeate Recycle", the disclosure of which is hereby incorporated by reference.

Water having a reduced caffeine content is conveyed through lines 56 and 60 back to water column 24 to be used for additional extraction of caffeine from supercritical carbon dioxide. The recycled water is preferably substantially free of caffeine and is brought to the desired pressure for extraction column 24 by an appropriate pump. Make-up water is added at 58 to offset any losses such as the water content of stream 54.

In the process of the present invention, water, the heavy phase, is contacted countercurrently with caffeine-rich supercritical carbon dioxide, the light phase, in water column 24 which is preferably an unpacked spray tower which is substantially open except for the presence of water inlet 38 and carbon dioxide inlet 26. Water level 28 is preferably maintained below $CO_2$ inlet 26 to insure that the water phase is discontinuous and the supercritical carbon dioxide phase is continuous. It has been found that the invention promotes exceptionally good mass transfer in extraction column 24. In this manner, it is possible to obtain very efficient extraction of caffeine from supercritical carbon dioxide.

Extraction in column 10 is preferably carried out at temperatures and pressures which favor extraction of caffeine from the moist coffee beans in column 10. Substantially the same temperatures and pressures will prevail in water column 24. In general, in the case of raw coffee solids, the temperature should not exceed about 135° C. Preferably, raw coffee solids are extracted at a temperature of from 70–140° C., more preferably 95–125° C. Aribica's or other quality coffee is extracted preferably at 95° to 105° C. and Robusta or other poorer flavored coffee at 115° C. to 135° C. Pressure in the extractor will also generally be high to favor extraction but not so high as to require excessively high equipment or operating costs. Generally, pressures of about 100 to 500 atmospheres are suitable, preferably about 150 to 350 atmospheres and most preferably 225–300 atmospheres for Arabic and 275 to 325 atmospheres for Robusta coffee.

The flow rate of carbon dioxide through water column 24 is preferably at least 200 ft$^3$ per hour per square foot of column cross sectional area and not more than the flow rate that would cause significant entrainment of the descending discontinuous water phase. In general, a flow rate of up to about 600 or 800 ft$^3$ per hour per square foot is suitable. The values mentioned are taken in an open area of the column and care should be taken that the flow rate is not so high that water entrainment occurs in the area of $CO_2$ inlet 28. Similarly, care must be taken to prevent entrainment in the area of water inlet 38.

The rate of water feed should be adjusted on the basis of the rate of supercritical carbon dioxide being fed to extraction column 24. Due to the equilibrium concentration between carbon dioxide, water and caffeine, it is desirable to maintain a weight ratio of supercritical carbon dioxide to water in extraction column 24 of at least 6:1. Accordingly, the water feed stream should be adjusted based on the rate of supercritical carbon dioxide feed to maintain this weight ratio. More preferably, the weight ratio of supercritical carbon dioxide to water should be maintained at between 8:1 and 16:1 and most preferably between 10:1 and 14:1.

Another important aspect of the present process which contributes to the efficient removal of caffeine from the supercritical carbon dioxide, as well as the high through-put rates of the present process, is the manner in which water is introduced into the top of spray column 24. In general, the water is introduced through a plurality of small apertures provided in the wall of a conduit grid such that a spray of water droplets of substantially uniform size is directed downwardly across substantially the entire cross sectional area of the column. The individual apertures are preferably circular in cross section, smooth walled, substantially perpendicular to the wall surfaces of the pipe in which they are provided, and oriented substantially vertically downwardly parallel to the substantially vertical orientation of water column 24. Each aperture is preferably not more than 1/10 inch in diameter, more preferably from 1/16 to 1/64 inch, and optimally about 1/32 inch. The height of the apertures, that is, the wall thickness of the conduit in which the apertures are provided, is of less importance but is generally not more than about ⅛ inch. A wall thickness of about 1/16 inches if generally suitable.

The number of apertures which are required is determined by the flow rate through the apertures, and the desired total water flow rate which in turn depends on the $CO_2$ flow rate and the desired ratio of $CO_2$ flow rate to water flow rate. As mentioned above, a $CO_2$ water ratio of about 6:1, preferably about 8–16:1 is suitable. In a typical installation, 100 to 400 apertures per square foot of column cross-section each aperture of 1/32" diameter are suitable to achieve the desired water flow rate. The size and uniformity of the water droplets will also be dependent on the rate of water flow through the apertures. In general, a water flow rate of at least about 100 ft/min is required for the aperture sizes mentioned above, and a suitable flow rate is from 150 to 5000 ft/minute. For apertures 1/32" diameter, a flow rate through the apertures of about 225 to 325 ft/min is particularly preferred.

The absorption column 24 of the present invention is an unpacked or open column and may be any suitable size depending upon the volume of caffeine recovery that is desired. By unpacked or open it is meant that the column is essentially open from end to end, that is, between the carbon dioxide inlet at the bottom of the column and the water inlet at its top. The column thus contains no packing, plates, flow restrictors, or flow impediments, other than water inlet 38 and $CO_2$ inlet 26. Gas distributor 26 is preferably located near the lower end of water column 24 but above the gas/liquid interface 28 and distributor 38 is preferably located near the upper end of column.

As mentioned above, the use of a specially designed water distributor 38 has been found to improve the overall efficiency of the present process. Referring now to FIG. 2, there is shown a top view of a preferred embodiment of distributor 38. Conduit tiers 42 and 44 can be seen in FIG. 2. Each tier 42, 44, includes a plurality of conduits 64 which are used to distribute water over a substantial cross-section of extraction column 24. As can be seen in FIG. 2, conduits 64 spread out across the cross-section of column 24. Each conduit 64 includes a plurality of apertures 66 (shown in FIG. 3). Water flows through water inlet 40 and into conduits 64 and thence out through apertures 66 into extraction column 24. These apertures act like a sparger to evenly distribute water throughout substantially the entire cross-sectional area of water column 24.

In order to achieve efficient separation of caffeine from the supercritical carbon dioxide which passes through column 24, it is preferred to inject the water into column 24 at a substantially uniform pressure and flow rate through each aperture 66 across substantially the entire cross-sectional area of extraction column 24. Since it is desirable to minimize the amount of column cross-section occupied by distributor 38, it is generally desirable to minimize the cross-section of conduit 66. This will tend to cause a relatively higher pressure drop along the length of each conduit 66. As a consequence, the pressure at which the water is injected into the water column will tend to decrease along the length of each conduit 66. In order to minimize this effect, distributor 38 may be provided with flow restriction means such as baffles 68. Instead of baffles 68, the flow restriction can be accomplished by a gradual narrowing of all of conduits 64 as the water gets farther from water inlet 40. Flow restriction means are known to those of ordinary skill in the art and any suitable known flow restriction means can be emPloyed to ensure that all of the water injected into extraction column 24 at a substantially uniform pressure.

One problem caused by the presence of a distributor 38 is that it physically restricts the flow space through which the supercritical carbon dioxide may flow in column 24. In general, it is desirable that distributor 38 occupy as little of the cross sectional area of the column as possible. In general, it will be necessary to occupy at least 10% of the cross sectional area, and occupying more than 50% should be avoided. Where a large amount of cross sectional area is occupied by distributor 38, it is preferred to arrange the conduits of the distributor in a plurality of tiers, preferably two tiers as shown in FIG. 2, with the conduits offset laterally to permit unimpeded downward flow of water through the apertures of each tier.

Figure 3:
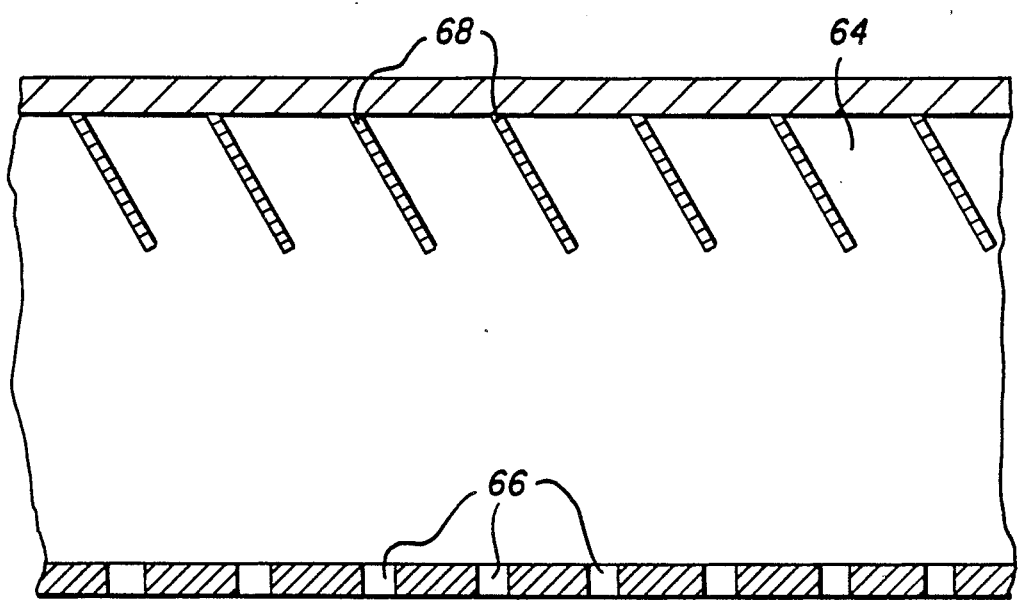
FIG. 3 is a cross-sectional view of a portion of a conduit of a distributor of the present invention.

Another element in the apparatus which contributes to the excellent performance of the present process is the particular design features of flow distributor 38 shown in FIG. 3. Referring now to FIG. 3, there is shown a side, cross-sectional side elevation view of a conduit 64. Conduit 64 includes suitable flow restriction means such as baffles 68 therein to maintain the water flowing out through apertures 66 at a relatively uniform pressure. Apertures 66 are vertically oriented to discharge water in a vertically downward direction. Apertures 66 are preferably of uniform cross-sectional area and have smooth, straight walls and are circular in cross-section s shown in FIG. 3. This is important because the physical characteristics of apertures 66 have a direct effect on the flow characteristics of water 48 in extraction column 24. Smooth, straight holes with round cross-section are the most preferred since they produce water flow with constant-sized water drops in a relatively uniform stream at relatively uniform pressure. These flow characteristics of the water positively contribute to the overall extraction achievable in extraction column 24.

The present invention provides excellent separation efficiency. Further, the low viscosity and low interfacial tension of supercritical carbon dioxide allow operation of the unpacked water column at flow rates much higher than normal liquid-liquid extraction columns. Thus, the throughput rate for the present absorption column is extremely high, particularly since the column contains no packing which obstructs fluid flow therein.

EXAMPLE 1

(Comparison)

Moist green Arabica coffee is added to an extraction vessel and supercritical $CO_2$ is recirculated through the coffee at a pressure and temperature of 300 bars and 100° C. respectively. The supercritical $CO_2$ is recirculated at a mass ratio of 88 lbs $CO_2$ per lb coffee. The $CO_2$ exits the bean column at a caffeine concentration of approximately 150 ppm and enters a water column [(4 inch inside diameter×40 ft. high)] packed with about 30 ft. of Glitsch 4AT-304 structured packing. Water is added to the top of the column at a mass ratio of 0.08 lbs water per lb $CO_2$. As the caffeine rich $CO_2$ flows up and around the wetted packing, caffeine is extracted into the water. The efficiency of caffeine removal from the coffee is 97.0% in 6.0 hours.

The efficiency of caffeine removal from the $CO_2$ into the water across the packed water column is 96.1%. The height of a theoretical stage in the water column is calculated to be 5.4 ft. This corresponds to about 5½ theoretical stages.

EXAMPLE 2

Moist green Arabica coffee is added to an extraction vessel and supercritical $CO_2$ is recirculated through the coffee at a pressure and temperature of 300 bars and 100° C. respectively as in Example 1. The supercritical $CO_2$ is recirculated at a mass ratio of 123 lbs $CO_2$ per lb coffee. The $CO_2$ exits the bean column at a caffeine concentration of approximately 93 ppm and enters the bottom of the water column of Example 1 but with the packing removed whereby water is added through a top distributor containing 1/32" diameter holes. The water pressure to the distributor is controlled to give a water velocity of 260 ft/min. The process ratio of water to $CO_2$ is 0.081 lbs water per lb $CO_2$. The efficiency of caffeine removal from the coffee is 97.3% in 6.0 hours. The efficiency of caffeine removal from the $CO_2$ into the water across the water column is 94.2%. The height of a theoretical stage in the water column is calculated to be 6.7 ft. This corresponds to about 4½ theoretical stages.

EXAMPLE 3

An additional run is made similar to Example 2 whereby the supercritical $CO_2$ pressure is lowered to 250 bars thereby having a decrease in mass ratio of $CO_2$/beans to 108 lbs $CO_2$ per lb coffee, with all other variables being constant. In this case the efficiency of caffeine removal from the coffee is 98.2% in 6.0 hrs. The efficiency of caffeine removal from the $CO_2$ into the water across the water column is 97.75%. The height of a theoretical stage in the water column is calculated to be 4.1 ft. This corresponds to about 7½ theoretical stages.

The foregoing description of the invention is for illustrative purposes only and the scope and content of the invention are to be determined by the claims appended hereto.

What is claimed is:

1. A process for the extraction of caffeine from supercritical carbon dioxide where separation efficiency is improved and is comparable to packed column performance for similar extraction systems which comprises countercurrently contacting water with caffeine-containing supercritical carbon dioxide in a column which is substantially open from end to end.

2. A process as claimed in claim 1 wherein the weight ratio of supercritical carbon dioxide to water in the extraction vessel is at least 6:1.

3. A process as claimed in claim 2 wherein the pressure in the column is from 1000 p.s.i. to about 6000 p.s.i.

4. A process as claimed in claim 3 wherein the velocity of the supercritical carbon dioxide through the column is about 200 to about 800 ft.$^3$/hr.-ft$^2$.

5. A process as claimed in claim 3 wherein the water enters the column through a plurality of apertures of equal size at a substantially uniform pressure.

6. A process as claimed in claim 5 wherein the water enters the column through said apertures at a velocity of at least 100 ft/min.

7. A process as claimed in claim 6 wherein the weight ratio of supercritical carbon dioxide to water in the extraction vessel is from about 8:1 to about 16:1.

8. In a process for the extraction of caffeine from supercritical carbon dioxide which comprises contacting a caffeine-containing material with a circulating stream of supercritical carbon dioxide to extract caffeine from the caffeine-containing material to produce a caffeine-rich stream of supercritical carbon dioxide, contacting the caffeine-rich stream of supercritical carbon dioxide countercurrently with water to extract caffeine from the circulating stream of supercritical carbon dioxide to produce a caffeine-depleted stream of supercritical carbon dioxide, and re-circulating the caffeine-depleted supercritical carbon dioxide stream to contact said caffeine-containing material to extract further caffeine therefrom, the improvement wherein said countercurrent contacting of said caffeine-rich stream of supercritical carbon dioxide with water is effected in a column which is substantially open from end to end where separation efficiency is improved and is comparable to packed column performance for similar extraction systems.

* * * * *